(12) United States Patent
Carlsson et al.

(10) Patent No.: US 7,790,102 B2
(45) Date of Patent: Sep. 7, 2010

(54) METHOD FOR PREPARING A MEDICAL SOLUTION FOR THE MANUFACTURE OF A MEDICAMENT FOR PERITONEAL DIALYSIS

(75) Inventors: Ola Carlsson, Lund (SE); Torbjörn Linden, Linderöd (SE); Anders Wieslander, Lund (SE)

(73) Assignee: Gambro Lundia AB (SE)

( * ) Notice: Subject to any disclaimer, the term of this patent is extended or adjusted under 35 U.S.C. 154(b) by 1156 days.

(21) Appl. No.: 10/538,777

(22) PCT Filed: Dec. 10, 2003

(86) PCT No.: PCT/SE03/01920

§ 371 (c)(1),
(2), (4) Date: Jun. 10, 2005

(87) PCT Pub. No.: WO2004/052268

PCT Pub. Date: Jun. 24, 2004

(65) Prior Publication Data

US 2006/0045794 A1    Mar. 2, 2006

Related U.S. Application Data

(60) Provisional application No. 60/432,580, filed on Dec. 10, 2002.

(30) Foreign Application Priority Data

Dec. 10, 2002    (SE) ................................. 0203671

(51) Int. Cl.
*A61L 2/08* (2006.01)

(52) U.S. Cl. ............................. 422/22; 422/28; 514/62
(58) Field of Classification Search .................. 422/28, 422/22; 514/62
See application file for complete search history.

(56) References Cited

U.S. PATENT DOCUMENTS

| 3,697,652 A | * | 10/1972 | Rovati et al. .................. 514/62 |
| 5,536,469 A | | 7/1996 | Jonsson et al. |
| 6,083,935 A | | 7/2000 | Wu et al. |

(Continued)

FOREIGN PATENT DOCUMENTS

WO    WO97/06810    2/1997

(Continued)

OTHER PUBLICATIONS

International Search Report for PCT/SE 2003/001920, dated Feb. 25, 2004.

(Continued)

*Primary Examiner*—Sean E Conley
(74) *Attorney, Agent, or Firm*—Finnegan, Henderson, Farabow, Garrett & Dunner LLP

(57) ABSTRACT

Method for preparing a medical solution, comprising the steps of a) providing a solution comprising one or more acetylated or deacetylated amino sugar/sugars in at least one compartment of a container at a pH from 2.5 to 5.0, and b) terminal sterilization of said at least one compartment and the contents therein, is disclosed, as well as a solution used for preparing the medical solution, a container containing said solution, and use of said solution for the manufacture of a medicament for peritoneal dialysis.

17 Claims, 6 Drawing Sheets

Inhibition of cell growth in a solution containing 1.5% NAG.

U.S. PATENT DOCUMENTS

2006/0046975 A1    3/2006    Carlsson et al.

FOREIGN PATENT DOCUMENTS

WO         WO99/27885         6/1999

OTHER PUBLICATIONS

International Search Report for PCT/SE 2003/001921, dated Feb. 25, 2004.

Office Action from U.S. Appl. No. 10/538,791 dated Feb. 28, 2008.
Office Action from U.S. Appl. No. 10/538,791 dated Aug. 11, 2008.
A. Breborowicz et al., "Replacement of Glucose with N-Acetylglucosamine in Peritoneal Dialysis Fluid—Experimental Study in Rats", Proceedings of the ISPD 2001 s365-s367—The IXth Congress of ISPD Jun. 26-29, 2001, Montreal, Canada.
Office Action from U.S. Appl. No. 10/538,791 dated Jan. 30, 2009.
The Merck Index, "Glucosamine," The Merck Index, $12^{th}$ Edition, 4466:758 (1996).

* cited by examiner

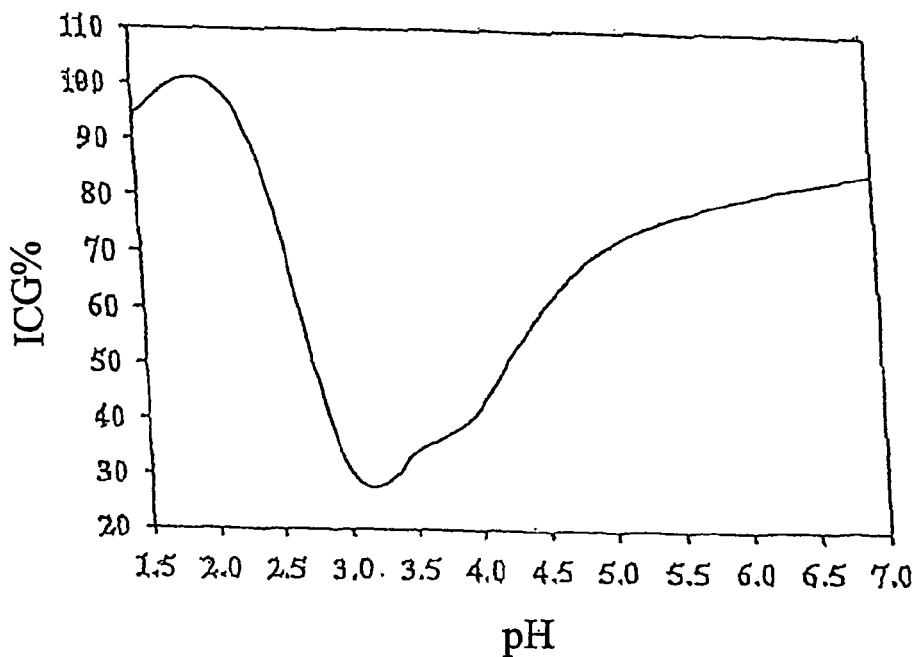
Figure 1. Inhibition of cell growth in a solution containing 1.5% NAG.
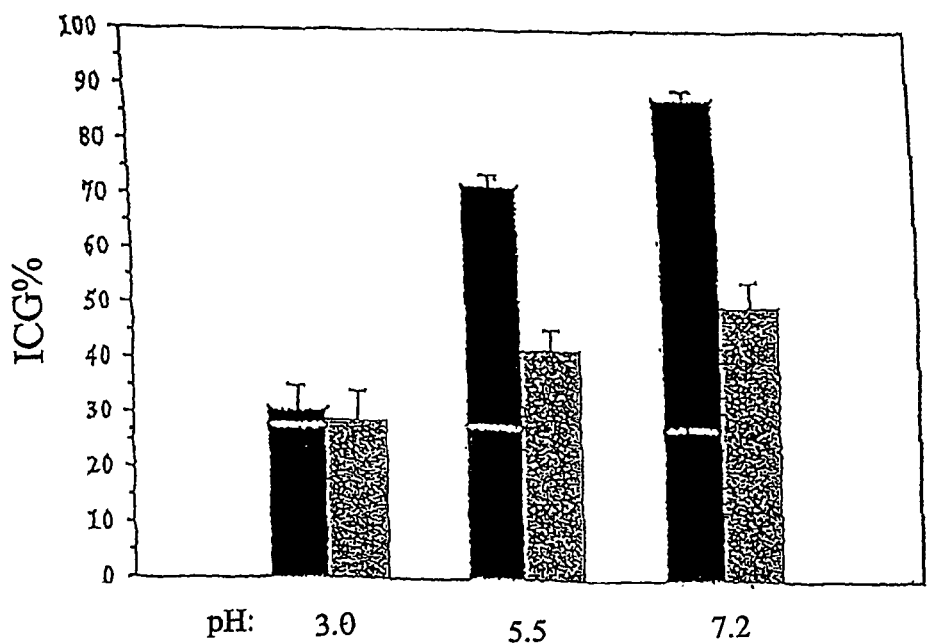
Figure 2. The effect of increased NAG concentration from 1.5% (black bars) to 30% (grey bars) for three different pH values.

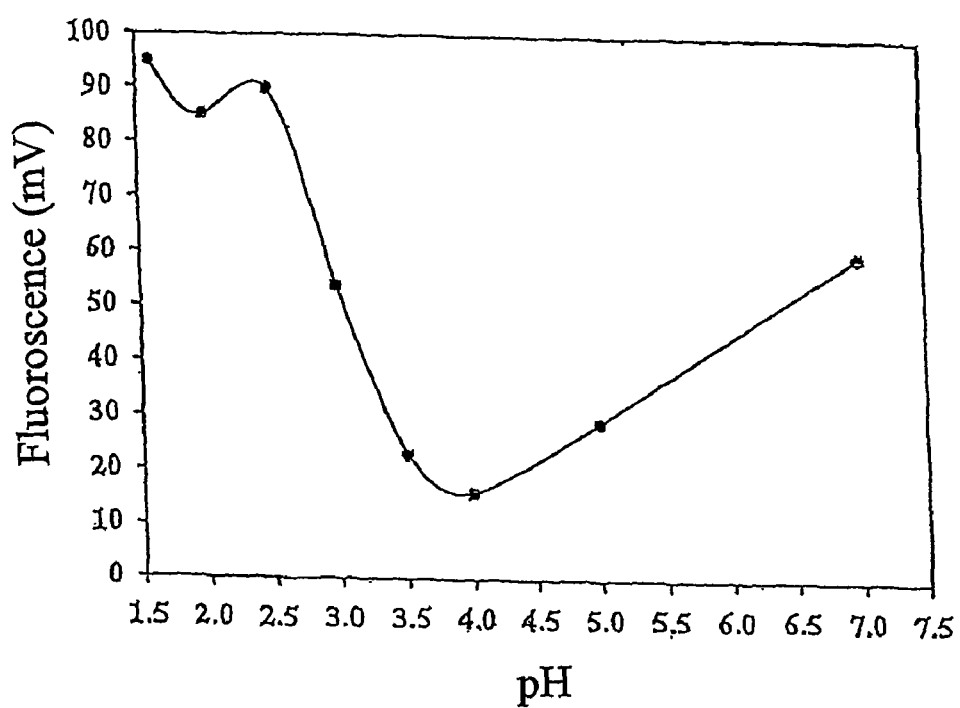
Figure 3. Fluorescence of heat sterilised NAG containing solutions at different pH.

METHOD FOR PREPARING A MEDICAL SOLUTION FOR THE MANUFACTURE OF A MEDICAMENT FOR PERITONEAL DIALYSIS

This application is a national phase under 35 U.S.C. §371 of international application number PCT/SE2003/001920, filed Dec. 10, 2003, which claims the benefit of priority to Swedish application number 0203671-3 filed Dec. 10, 2002, and U.S. Provisional Application 60/432,580, filed Dec. 10, 2002.

BACKGROUND OF THE INVENTION

The present invention relates to a method for preparing a medical solution, a solution used for preparing the medical solution, a container containing said solution, and use of said solution for the manufacture of a medicament for peritoneal dialysis.

BACKGROUND ART

N-acetylglucosamine (NAG) and glucosamine are biochemically classified as amino sugars. Amino sugars are formed in almost all cells from blood glucose through a series of biochemical reactions. Hyaluronan is a polymer composed of dimers containing N-acetylglucosamine and glucuronic acid. It has been shown that the function of the peritoneum as a dialysis membrane is better preserved in rats that have been chronically dialyzed with fluid supplemented with exogenous hyaluronan (see Wieczorowska K, Breborowicz A et al, Protective effect of hyaluronic acid against peritoneal injury, Perit Dial Int 1995; 15:81-83).

Breborowicz A, Kuzlan-Pawlaczyk M et al, The Effect of N-Acetyl-glucosamine as a Substrate for In Vitro Synthesis of Glycosaminoglycans by Human Peritoneal Mesothelial Cells and Fibroblasts, Advances in Peritoneal Dialysis, 1998; 14:31-35, teaches that NAG rapidly stimulates the production of hyaluronan and sulphated glycosaminoglycans by human peritoneal mesothelial cells and fibroblasts.

Wu G, Wieczorowska-Tobis K, et al, N-acetylglucosamine changes permeability of peritoneum during chronic peritoneal dialysis in rats, Perit Dial Int, 1998; 18:217-224 concludes that peritoneal dialysis with a dialysis solution supplemented with N-acetylglucosamin causes accumulation of glucosaminoglycans in the peritoneal interstitium, resulting in a favorable change of the peritoneal permeability.

Breborowicz, M et al discloses replacement of glucose with N-acetylglucosamine in peritoneal dialysis fluid.

U.S. Pat. No. 5,536,469 discloses a system employing a sterile medical solution containing glucose or glucose-like compounds and a solution intended for said system.

Due to its advantageous characteristics, NAG has been introduced as a component in peritoneal dialysis solutions replacing part or all of the glucose component with a view to obtaining a more biocompatible peritoneal dialysis solution (see WO97/06810).

Peritoneal dialysis is a method for exchanging solutes and water in capillary vessels of a patient's peritoneum with hypertonic solution, which is infused into the peritoneal cavity. The principle of this method is diffusion of solutes transferred according to the concentration gradient and water migration due to osmotic differences. This method has many advantages, e.g. that no special apparatus is commonly required. It gives less influence on the hemodynamics because extracorporeal circulation of the patient's blood is not necessary, and further the peritoneal dialysis is a continuous treatment and therefore more similar to the function of the kidneys.

Peritoneal dialysis is usually classified as continuous ambulatory peritoneal dialysis (CAPD), intermittent peritoneal dialysis (IPD), continuous cyclic peritoneal dialysis (CCPD) or automated peritoneal dialysis (APD).

In CAPD a catheter is permanently implanted in the abdominal wall of the patient and about 1.5 to 2.5 l of the dialysis fluid is normally introduced via the catheter into the peritoneal cavity. The peritoneal cavity is flooded with this fluid, left for an appropriate lapse of time and then drained. Removal of solutes and water takes place across the peritoneum, which acts as a semipermeable membrane.

The dialysis fluid normally used for peritoneal dialysis is an aqueous solution comprising an osmotic agent such as glucose and the like, electrolytes such as sodium, potassium, calcium, magnesium, and organic acid salts such as sodium lactate, sodium bicarbonate, or sodium pyruvate. The components of these peritoneal dialysis fluids are selected to control the levels of electrolytes or the acid-base equilibrium, to remove waste materials and to efficiently carry out ultrafiltration.

It is known to pack medical solutions in multicompartment bags from e.g. WO 99/27885 (Gambro Lundia AB), in which different solutes may be kept in separate compartments of the bag with a view to, inter alia, regulating the concentration of active ingredients in the finally prepared solution.

Medical fluids are normally sterilised by heat. Medical authorities in many countries require sterilisation after final packaging of the medical product. It is therefore often not possible to sterile filter the solution.

However, a problem with the formation of undesired cytotoxic products during heat sterilisation and storage exists for a variety of medical solutions, inter-alia within the dialysis area, e.g. for peritoneal dialysis solutions. It is known e.g. from EP-B1-0 668 785 (Gambro Lundia AB) to reduce the amount of toxic degradation products from glucose or glucose-like compounds in a medical solution.

It has now been found that also amino sugars, e.g. NAG, in conventional medical solutions exhibit an increased cytotoxicity after heat sterilisation. This cytotoxicity depends on the formation of toxic degradation products from said amino sugars. In contact to glucose, none of the known glucose degradation products has been found in heat sterilised NAG solutions. This fact has not been known previously and forms the basis for the present invention.

NAG and other amino sugars have a major difference from glucose and glucose-like compounds by having one amino group and possibly an acetyl group coupled to the glucose ring. Regarding the degradation process, it has been found that the pH of a NAG solution increases during sterilisation while in the case of glucose it decreases during sterilisation. This indicates that NAG is, in contrast to glucose, degraded by a hydrolysis that forms acetate, which increases the pH.

Thus, there is a need to solve the above defined problem and to provide a medical solution containing amino sugars, in particular NAG, and derivatives thereof and at the same time having the ability to be heat sterilised without the formation of the above-mentioned cytotoxic products.

SUMMARY OF THE INVENTION

The object of the present invention is to solve the above-mentioned problem.

According to the present invention this object is achieved by an improved method for preparing a medical solution, preferably a peritoneal dialysis solution, comprising the steps of:
a) providing a solution comprising one or more acetylated or deacetylated amino sugars in at least one compartment of a container, said solution having a pH of 2.0-5.0, and
b) terminal sterilisation of said at least one compartment and the contents therein.

Further, the present invention relates to the solution used for preparing the medical solution, and to a container containing said solution.

The present invention also relates to use of said solution for the manufacture of a medicament for peritoneal dialysis.

In another aspect the present invention relates to a method of performing peritoneal dialysis, wherein said method comprises the introduction of said medicament for peritoneal dialysis into the peritoneal cavity of a patient.

Further disclosure of the objects, problems, solutions and features of the present invention will be apparent from the following detailed description of the invention with reference to the drawings and the appended claims.

BRIEF DESCRIPTION OF THE DRAWINGS

FIG. 1 is a graph showing the relationship between pH and inhibition of cell growth (ICG) in a solution containing 1.5% NAG.

FIG. 2 is a bar diagram showing the effect of increased NAG concentration of 1.5% and 30% for three different pH values.

FIG. 3 is a graph showing the fluorescence of heat sterilised NAG containing solutions at different pH values.

DETAILED DESCRIPTION OF PREFERRED EMBODIMENTS

Figure 4A:
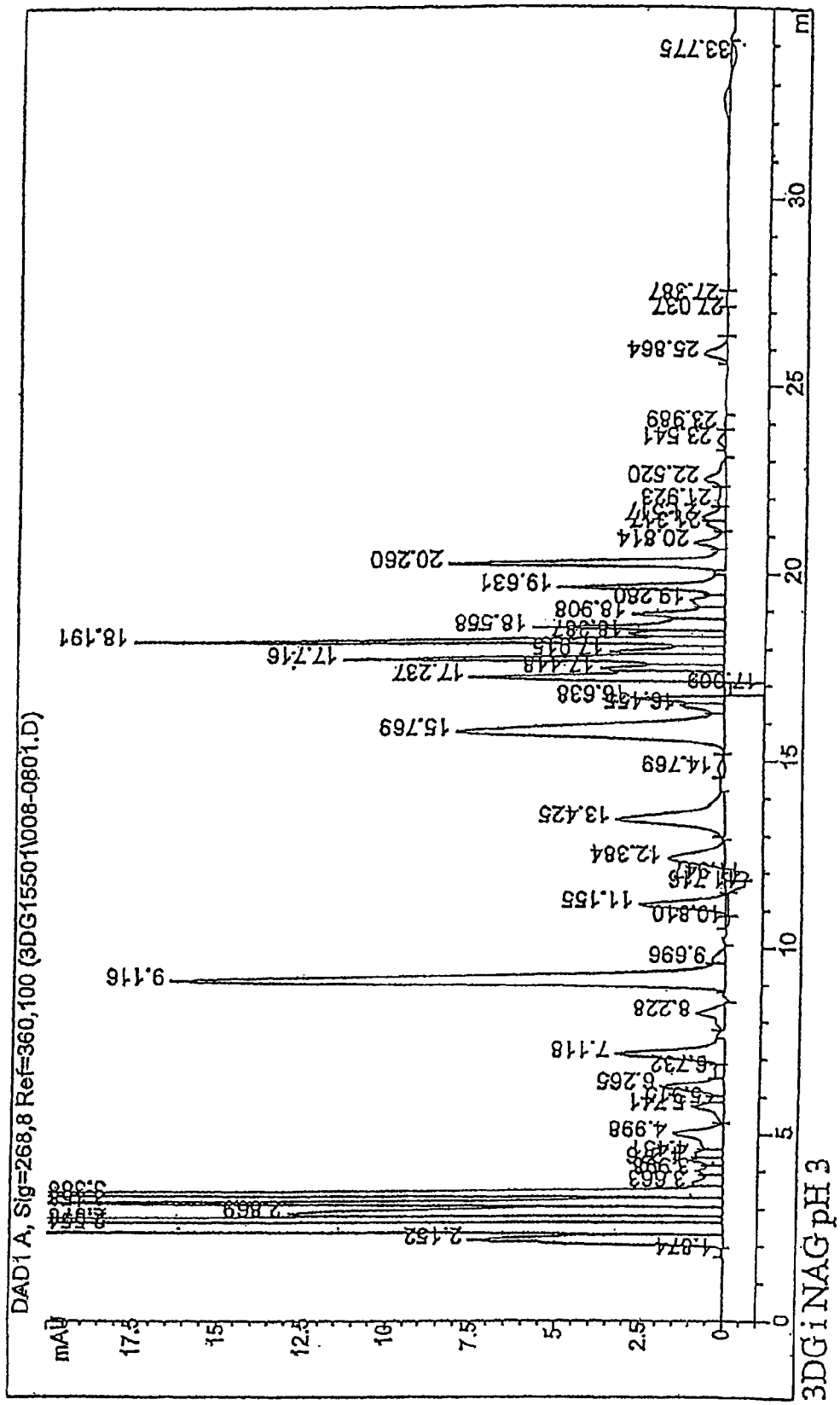
FIGS. 4a-4d are HPLC chromatograms showing the different decomposition patterns between a heat sterilised NAG solution and a heat sterilised glucose solution.

The present invention is a development of the above mentioned teachings and relates to a method for preparing a sterile medical solution, preferably a solution for peritoneal dialysis.

Experiments in which measurements of the percentage of inhibition of cell growth (ICG) and fluorescence have been made at varying pH values and NAG concentrations during terminal heat sterilisation are illustrated in FIGS. 1-3. The results of the experiments imply that the pH of the amino sugar containing solution should be decreased from the neutral level and that, in a preferred embodiment of the invention, also the concentration of the amino sugar/sugars should be optimised.

A simple, reliable and known way to study the cytotoxicity of substances or of medical fluids is to test proliferation as in vitro inhibition of cell growth (ICG) in cultured cells. Another method to get a rough estimation of the amount of amino sugars that is rearranged is measurement of the fluorescence.

More precisely, from the graph in FIG. 1 it can be seen that the inhibition of cell growth reaches a minimum with sterilisation around pH 2.5-3.5 in a solution containing 1.5% NAG. This implies that a NAG containing solution sterilised at an optimal pH around 2.5-3.5 from an in vitro toxicological point of view is more compatible for humans than solutions giving a higher percentage of inhibited growth when sterilised at higher or lower pH values.

The bar diagram in FIG. 2 illustrates the effect of increased NAG concentration at different pH values during terminal heat sterilisation. It can be seen that the percentage inhibition of cell growth is lower after terminal heat sterilisation at a pH of 3.0 than at a pH of 5.5 and 7.2, and that the inhibition of cell growth is lower after a terminal heat sterilisation at a NAG concentration of 30% than at a NAG concentration of 1.5% for all three pH values.

FIG. 3 shows the relationship between pH for a terminally heat sterilised NAG containing solution and the fluorescence, measured at an excitation at 350 nm and an emission of 430 nm. The lowest fluorescence is seen at around pH 4, which corresponds well with the toxicity result shown in FIG. 1.

The term "terminal" sterilisation used herein is intended to mean that the product is sterilised in its final package by a sterilisation method involving addition of energy, e.g. heating and/or radiation (see also European Pharmacopoeia 1977, p 283, col 1, last paragraph, to col 2, first paragraph, and p 284, col 2, "Filtration", for a detailed description of this term, as well as for a review of different sterilisation techniques). Sterile filtration involves filtration of the solution to be included in the product, and the solution is aseptically filled into the container. This does not secure the sterility required in this context, and sterile filtration can therefore not be used as a sterilisation method for a medicament if it is possible to sterilise the medicament by terminal sterilisation.

The terminal sterilisation may include heat sterilisation and/or radiation sterilisation, but is preferably heat sterilisation effected in an autoclave at a temperature of at least 100° C., preferably at 121° C. The sterilisation time may vary depending on the sterilisation temperature, the type of container and the contents therein to be sterilised. The radiation sterilisation may be either ionizing or non-ionizing sterilisation. Examples of ionising sterilisation are gamma and beta radiation. An example of non-ionizing radiation sterilisation is UV radiation.

The method according to the present invention is preferably effected for a multicompartment container as disclosed in WO 99/27885 (Gambro AB). In the present invention, such a container comprises at least one compartment containing a physiologically compatible pH adjusting and diluting solution as well as at least one compartment containing a solution comprising one or more acetylated or deacetylated amino sugars, in the following called amino sugar solution for simplicity. The amino sugar solution may be present in only one compartment. The solutions in the different compartments are heat sterilisable, and the whole container can be heat sterilised in an autoclave with the solutions in situ in said compartments. The solutions in the separated compartments, which are delimited from each other during the sterilisation and the subsequent storage, can be mixed after sterilisation to form a finally prepared sterile medical solution, preferably a solution for peritoneal dialysis. It may also be mixed with a terminally sterilised pH adjusting and diluting solution in at least one other terminally sterilised compartment of the container, thereby finally preparing the medical solution. Such a medical solution may be stored after terminal sterilisation up to longer periods of time before mixing with the terminally sterilised pH adjusting and diluting solution. The terminal sterilisation can however also be effected for separated interconnectable containers comprising the solutions to sterilise and provided with connection means with sterile connecting valves for sterile connection. The separated containers can also be connected already during manufacture by means of a breakable seal, for example a conventional frangible pin.

According to the invention, the pH of the amino sugar containing solution is 2.0-5.0. In one preferred embodiment of the invention the pH of the amino sugar containing solution is preferably 2.5-3.5, most preferably 3.0, so that the formation of cytotoxic substances during the terminal sterilisation step is substantially prevented.

In another embodiment of the invention the amino sugar in the amino sugar containing solution having a pH of 2.0-5.0 in one or more of said compartments is present in a concentration of 15-40% by weight, preferably 20-40% by weight, most preferably at least 30% by weight, with the basis on the solution in each of said compartments, e.g. 15, 20, 25, 30, 35, and 40% by weight. Preferably, said amino sugar is N-acetylglucosamine (NAG).

The upper limit for the concentration for each amino sugar in the solution is determined by its solubility therein. The compartment comprising the amino sugar containing solution may also contain any organic acid or other pH stabilising agent in order to further stabilise the pH during sterilisation. The solutions of the different compartments have such respective pH values, concentrations and volumes that the finally prepared medical solution after mixing the solutions of the compartments has a pH that is substantially neutral, i.e. a pH between 6.0 and 8.0, preferably about 7.4, and an amino sugar concentration between 0.2 and 15.0%, preferably 0.5-6.0%, e.g. 0.5-2.0% by weight, with the basis on the finally prepared solution.

The volume of each compartment, as well as the proportion between the compartments, is in practice not critical. Each compartment volume depends on the volume of constituent to be present therein. In the most preferred embodiment, the compartment which accommodates the pH adjusting and diluting solution is larger than the compartment which accommodates the amino sugar containing solution and is also the compartment in which the solution/solutions from the other compartments is/are mixed with the pH adjusting and diluting solution.

In a preferred embodiment the medicament to be prepared is a peritoneal dialysis solution containing N-acetylglucosamine and having a pH of 7.4.

Figure 4B:
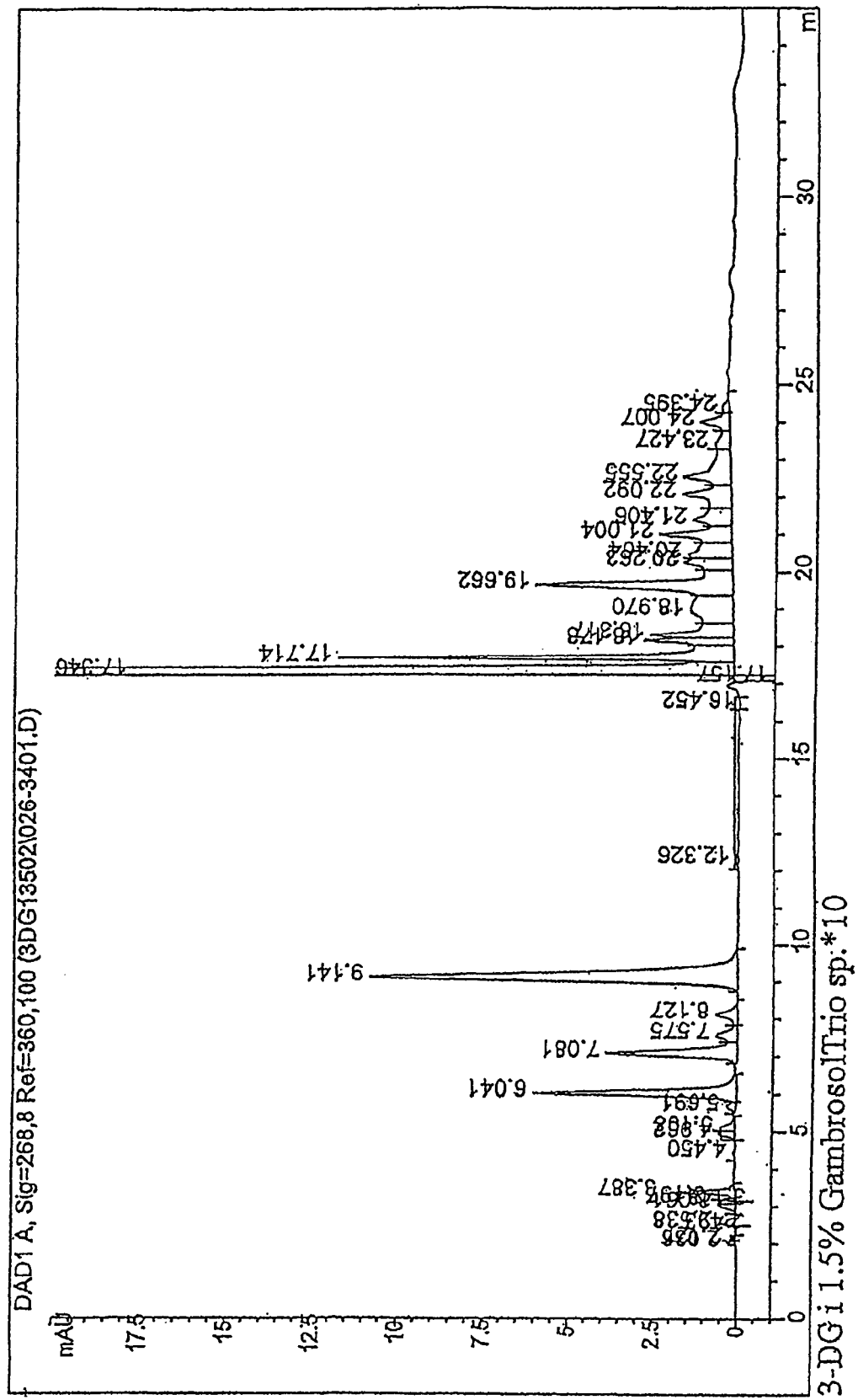
Figure 4C:
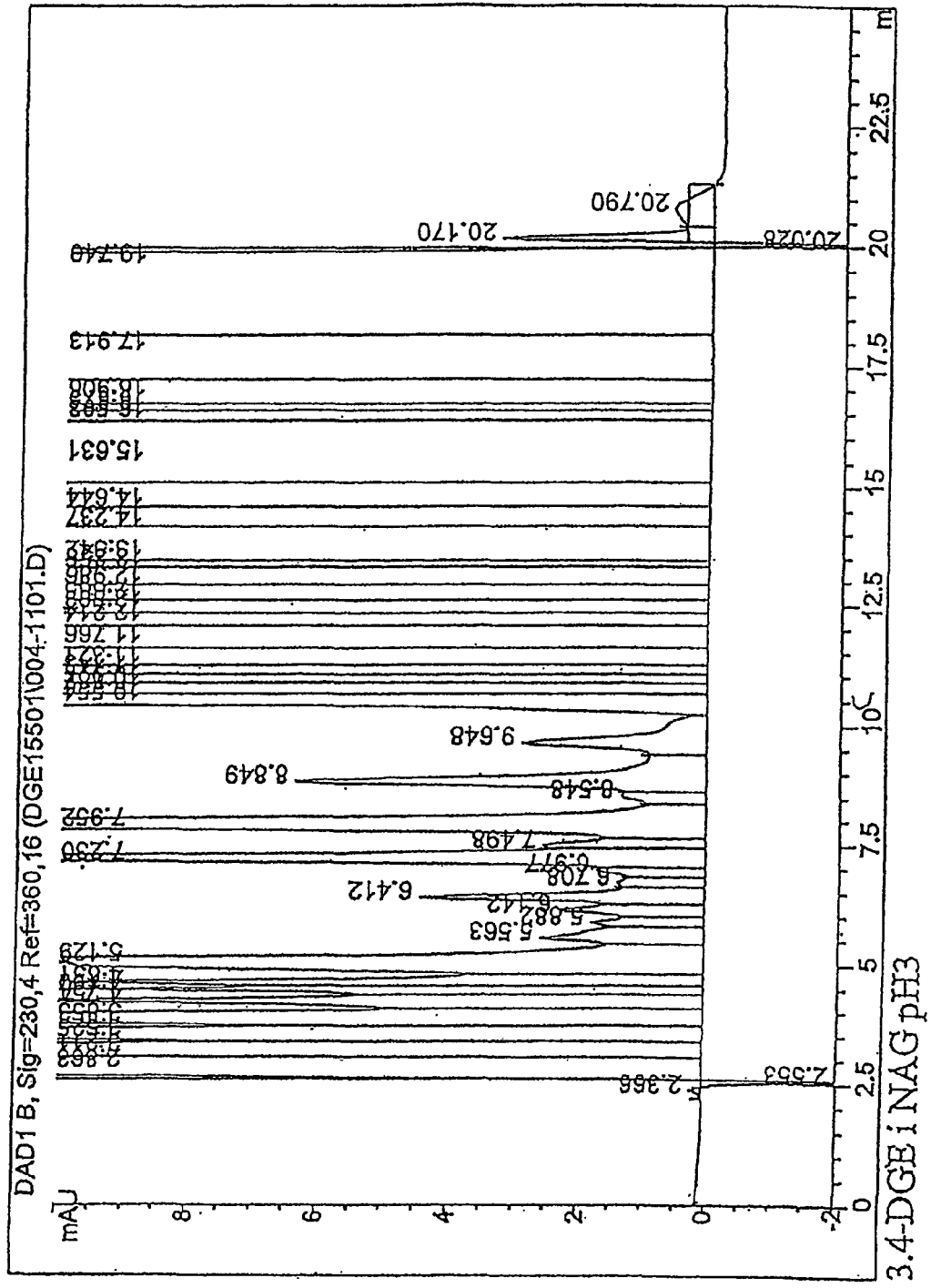
Figure 4D:
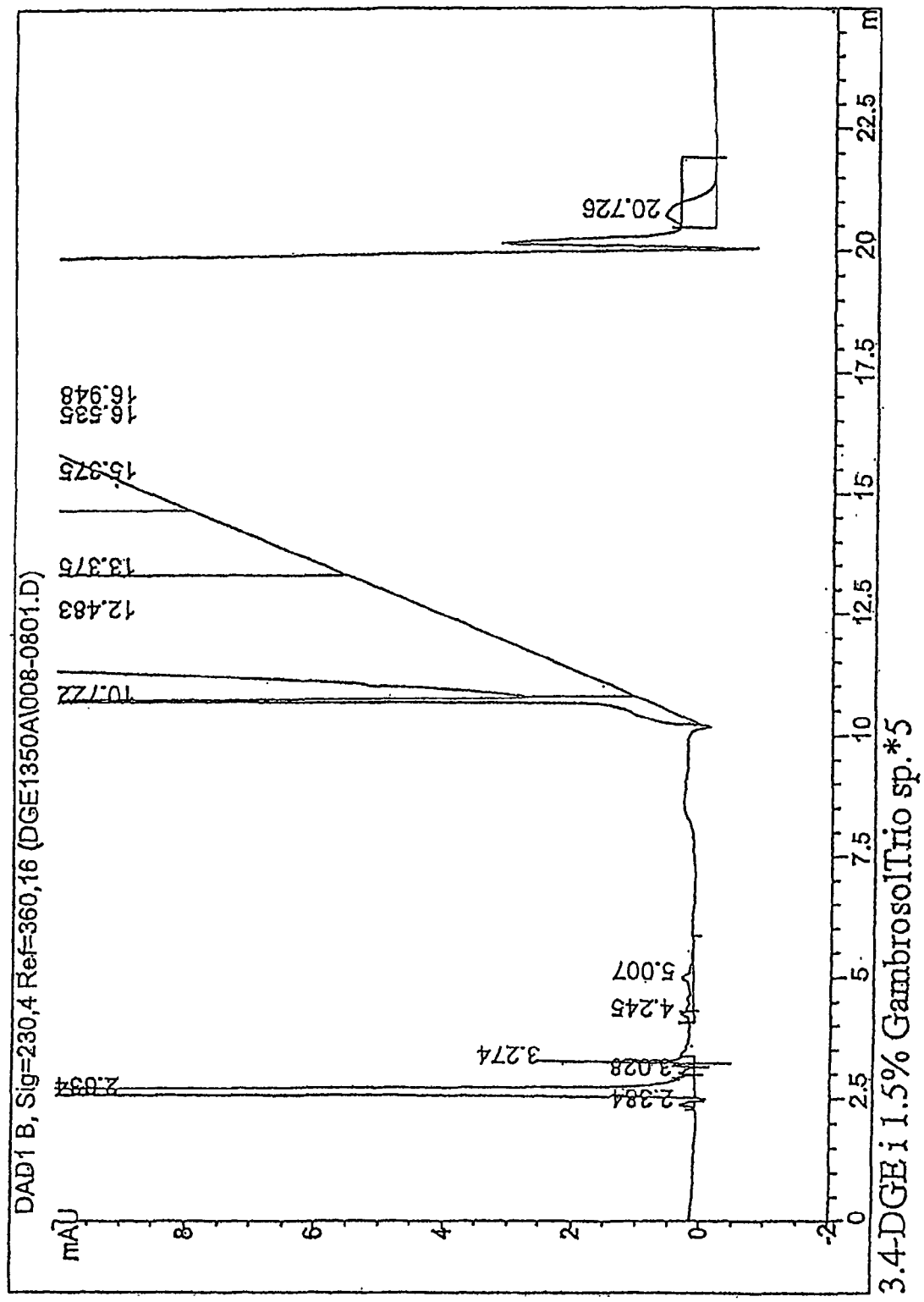

It should be noted that the decomposition pattern for an amino sugar solution during heat sterilisation follows specific Maillard reactions giving several different toxic decomposition products. The decomposition pattern differs for e.g. a glucose solution during heat sterilisation, wherein different decomposition products are formed. This difference is illustrated in FIGS. 4a-4d, showing chromatograms when analysing 3-DG and 3,4-DGE in a NAG solution and in a glucose solution, respectively. The difference in degradation is likely due to that the NAG molecules contains groups that allows the Maillard reaction to take place and therefore create a large number of degradation products not seen in a glucose solution.

The term "amino sugar containing solution" used herein means a solution comprising one or more acetylated or deacetylated amino sugars involved in the present invention chosen from N-acetylglucosamine (NAG), galactosamine, N-acetylgalactosamine, mannosamine, and N-acetylmannosamine in the form of monomers, oligomers and/or polymers thereof including chitin, and human glucosaminoglycans, as well as derivatives thereof. The most preferred amino sugar is N-acetylglucosamine (NAG). Thus, the acetylated or deacetylated amino sugars may be represented by only one of the amino sugars listed or by a combination thereof as well as derivatives thereof.

The term "derivatives thereof" used herein means derivatives of said amino sugars having the same or essentially the same ability to form cytotoxic degradation products during sterilisation.

The term "pH adjusting and diluting solution" used herein means a solution to be mixed with, e.g. acting as a receiving medium for, the amino sugar containing solution and at the same time a solution adjusting the pH of the solution after mixing with the amino sugar containing solution to essentially neutral, i.e. with a pH between for example 6.0 and 8.0, preferably about 7.4.

The term "low levels of cytotoxic degradation products" used herein means that the amount of degradation products from the amino sugars is so low in the medical solution prepared according to the present invention that it is not more toxic to cultured cells than dialysis solutions according to prior art.

The pH adjusting and diluting solution in the preferred embodiment contains pH adjusting agents, such as salts of inorganic acids, organic acids, alkalic substances etc. in a pharmaceutically stable range. Inorganic acids include hydrochloride acid etc., organic acids include lactic acid, malic acid, acetic acid, succinic acid, maleic acid, pyruvic acid, citric acid, gluconic acid, etc., and alkalic substances include sodium hydrate, sodium bicarbonate etc. Also, various amino acids can be used as a pH-adjusting agent.

After sterilisation the amino sugar containing solution is finally prepared for use by mixing it with the pH adjusting and diluting solution, optionally with solutions in other compartments of the container. The medical solution, preferably a peritoneal dialysis solution, thus obtained may also comprise different electrolyte ions, e.g. sodium, potassium, calcium, magnesium, chloride, lactate, and bicarbonate ions, in concentrations which are biocompatible and substantially isotonic. The electrolytes may be originally present in the pH adjusting and diluting solution, the amino sugar containing solution and/or another solution in one or more other compartments of the container, depending on their compatibility during sterilisation and storage, normally in the form of pharmaceutically acceptable salts. The amount of cations in a peritoneal dialysis solution ready for use is generally 110 to 140 mEq/ml of sodium ions, 0 to 0.05 mEq/l of potassium ions, 0 to 3 mEq/l of magnesium ions and 0 to 6 mEq/l of calcium ions. Preferably the amount of chloride ions is 80 to 144 mEq/l.

The peritoneal dialysis solution as a preferred embodiment of the medical solution according to the present invention may also comprise other physiologically compatible constituents, e.g. further osmotic agents, such as carbohydrates, preferably glucose, proteins and peptides, preferably albumin, as well as antioxidants, such as bisulphite.

The peritoneal dialysis solution of the present invention described above is applicable not only to continuous ambulatory peritoneal dialysis (CAPD) but also to intermittent peritoneal dialysis (IPD), continuous cyclic peritoneal dialysis (CCPD), and automated peritoneal dialysis (APD). Moreover, it contains low levels of cytotoxic degradation products from amino sugars.

The present invention also relates to a solution as such having the above defined characteristics.

The present invention also relates to a container containing the amino sugar containing solution in at least one compartment, wherein said solution has been sterilised and contains low levels of cytotoxic degradation products.

Further, the present invention relates to use of the solution according to the present invention for the manufacture of a medicament for peritoneal dialysis, wherein it is mixed with a sterilised pH adjusting and diluting solution.

As stated above, the present invention also relates to a method of performing peritoneal dialysis, wherein said method comprises the introduction of said medicament for peritoneal dialysis into the peritoneal cavity of a patient.

In order to illustrate different embodiments of the present invention, containers having different compartment constructions containing the constituents for the preparation of a peritoneal dialysis solution will be described in the Examples below, as well as the composition of the solutions in each compartment. In the examples, N-acetylglucoseamine (NAG) is used as amino sugar, either in one or two compartments of the container. The pH for the NAG containing solutions in each compartment varied between 2.0 and 5.0 before mixing and between 6.0 and 8.0 in the finally prepared medical solution.

EXAMPLES

Example 1

| Compartment A | Volume | 100 | ml |
| | Sodium | 0-140 | mM |
| | NAG | 300 | g/l |
| Compartment B | Volume | 180 | ml |
| | Sodium | 0-140 | mM |
| | NAG | 300 | g/l |
| Compartment C | Volume | 1900 | ml |
| | Sodium | 0-140 | mM |
| | Lactate | 40 | mM |
| | Magnesium | 0.25-0.75 | mM |
| | Calcium | 0.9-2.0 | mM |

Final composition when the contents of compartments A+C are mixed:

| Volume | 2000 | ml |
| Sodium | 0-140 | mM |
| NAG | 15 | g/l |
| Lactate | 38 | mM |
| Magnesium | 0.24-0.71 | mM |
| Calcium | 0.85-1.9 | mM |

Final composition when the contents of compartments B+C are mixed:

| Volume | 2080 | ml |
| Sodium | 0-140 | mM |
| NAG | 26 | g/l |
| Lactate | 36.5 | mM |
| Magnesium | 0.22-0.68 | mM |
| Calcium | 0.82-1.8 | mM |

Final composition when the contents of compartments A+B+C are mixed:

| Volume | 2180 | ml |
| Sodium | 0-140 | mM |
| NAG | 38.5 | g/l |
| Lactate | 34.9 | mM |
| Magnesium | 0.21-0.65 | mM |
| Calcium | 0.78-1.7 | mM |

Example 2

| Compartment A | Volume | 100 | ml |
| | Sodium | 0-140 | mM |
| | NAG | 300 | g/l |
| Compartment B | Volume | 180 | ml |
| | Sodium | 0-140 | mM |
| | Glucose | 500 | g/l |
| Compartment C | Volume | 1900 | ml |
| | Sodium | 0-140 | mM |
| | Lactate | 40 | mM |
| | Magnesium | 0.25-0.75 | mM |
| | Calcium | 0.9-2.0 | mM |

Final composition when the contents of compartments A+C are mixed:

| Volume | 2000 | ml |
| Sodium | 0-140 | mM |
| NAG | 15 | g/l |
| Glucose | 0 | g/l |
| Lactate | 38 | mM |
| Magnesium | 0.24-0.71 | mM |
| Calcium | 0.86-1.9 | mM |

Final composition when the contents of compartments A+B+C are mixed:

| Volume | 2100 | ml |
| Sodium | 0-140 | mM |
| NAG | 14.3 | g/l |
| Glucose | 23.8 | g/l |
| Lactate | 36 | mM |
| Magnesium | 0.23-0.68 | mM |
| Calcium | 0.81-1.8 | mM |

Example 3

| Compartment A | Volume | 60 | ml |
| | Sodium | 0-140 | mM |
| | NAG | 165 | g/l |
| | Glucose | 330 | g/l |
| Compartment B | Volume | 100 | ml |
| | Sodium | 0-140 | mM |
| | NAG | 165 | g/l |
| | Glucose | 330 | g/l |
| Compartment C | Volume | 1900 | ml |
| | Sodium | 0-140 | mM |
| | Lactate | 40 | mM |
| | Magnesium | 0.25-0.75 | mM |
| | Calcium | 0.9-2.0 | mM |

Final composition when the contents of compartments A+C are mixed:

| Volume | 1960 | ml |
| Sodium | 0-140 | mM |
| NAG | 5.1 | g/l |
| Glucose | 10.1 | g/l |
| Lactate | 38.8 | mM |
| Magnesium | 0.24-0.73 | mM |
| Calcium | 0.87-1.9 | mM |

Final composition when the contents of compartments B+C are mixed:

| | | |
|---|---|---|
| Volume | 2000 | ml |
| Sodium | 0-140 | mM |
| NAG | 8.25 | g/l |
| Glucose | 16.5 | g/l |
| Lactate | 38.0 | mM |
| Magnesium | 0.24-0.71 | mM |
| Calcium | 0.86-1.9 | mM |

Final composition when the contents of compartments A+B+C are mixed:

| | | |
|---|---|---|
| Volume | 2060 | ml |
| Sodium | 0-140 | mM |
| NAG | 12.8 | g/l |
| Glucose | 25.6 | g/l |
| Lactate | 37 | mM |
| Magnesium | 0.23-0.69 | mM |
| Calcium | 0.83-1.8 | mM |

Example 4

| | | | |
|---|---|---|---|
| Compartment A | Volume | 1000 | ml |
| | NAG | 10 | g/l |
| | Glucose | 20 | g/l |
| | Magnesium | 0.48-1.46 | mM |
| | Calcium | 1.8-4.0 | mM |
| Compartment B | Volume | 1000 | ml |
| | Sodium | 0-140 | mM |
| | Bicarbonate | 165 | g/l |

Final composition when the contents of compartments A+B are mixed:

| | | |
|---|---|---|
| Volume | 2000 | ml |
| Sodium | 0-140 | mM |
| NAG | 5 | g/l |
| Glucose | 10 | g/l |
| Bicarbonate | 37.5 | mM |
| Lactate | 2.5 | mM |
| Magnesium | 0.24-0.73 | mM |
| Calcium | 0.9-2.0 | mM |

The invention has been described above with reference to preferred embodiments of the invention. A skilled person will recognise that further combinations are possible. Modifications which are apparent to a skilled person are intended to be incorporated within the scope of the invention, which is limited only by the appended claims.

The invention claimed is:

1. A method for preparing a medical solution, comprising the steps of:
   a) providing a solution comprising one or more acetylated or deacetylated amino sugars in at least one compartment of a container, said solution having a pH of 2.5-3.5, and
   b) terminally sterilizing of said at least one compartment and the solution therein to form a terminally sterilized solution, wherein the terminally sterilized solution contains low levels of cytotoxic degradation products; and wherein the one or more acetylated or deacetylated amino sugars is N-acetylglucosamine.

2. The method according to claim 1, wherein said N-acetylglucosamine is present in a concentration of 15-40% by weight with respect to the weight of the solution in said at least one compartment.

3. The method according to claim 2, wherein said N-acetylglucosamine is present in a concentration of 20-40% by weight with respect to the weight of the solution in said at least one compartment.

4. The method according to claim 3, wherein said N-acetylglucosamine is present in a concentration of at least 30% by weight with respect to the weight of the solution in said at least one compartment.

5. The method according to claim 1, wherein the terminal sterilisation is heat sterilisation at a temperature of at least 100° C.

6. The method according to claim 5, wherein the terminal sterilisation is heat sterilisation at a temperature of 121° C.

7. The method according to claim 1, wherein each compartment of the container is delimited from other compartments during the terminal sterilisation, and wherein the terminally sterilised solution containing N-acetylglucosamine is mixed with a terminally sterilised pH adjusting and diluting solution in at least one other terminally sterilised compartment of the container, thereby finally preparing the medical solution.

8. The method according to claim 7, wherein the pH in the finally prepared medical solution is 6.0-8.0.

9. The method according to claim 8, wherein the pH in the finally prepared medical solution is 7.4.

10. The method according to claim 7, wherein the concentration of N-acetylglucosamine in the finally prepared solution is 0.2-15.0% by weight.

11. The method according to claim 10, wherein the concentration of N-acetylglucosamine in the finally prepared solution is 0.5-6.0% by weight.

12. The method according to claim 1, wherein physiologically compatible constituents in the form of carbohydrates, proteins, peptides, and antioxidants are present in one or more of said compartments.

13. The method according to claim 12, wherein the carbohydrate is glucose.

14. The method according to claim 1, wherein the medical solution prepared is a peritoneal dialysis solution.

15. The method according to claim 1, wherein the pH is 3.0.

16. The method according to claim 1, wherein the terminal sterilisation is radiation sterilisation.

17. A method for preparing a medical solution, comprising the steps of:
   a) providing a solution comprising one or more acetylated or deacetylated amino sugars in at least one compartment of a container, said solution having a pH of 2.5-3.5, and
   b) terminally sterilizing of said at least one compartment and the solution therein to form a terminally sterilized solution, wherein the terminally sterilized solution results in lower levels of inhibition of cell growth compared to a solution terminally sterilized at a pH outside the range of 2.5-3.5, and wherein the one or more acetylated or deacetylated amino sugars is N-acetylglucosamine.

* * * * *

UNITED STATES PATENT AND TRADEMARK OFFICE
CERTIFICATE OF CORRECTION

PATENT NO. : 7,790,102 B2
APPLICATION NO. : 10/538777
DATED : September 7, 2010
INVENTOR(S) : Ola Carlsson et al.

It is certified that error appears in the above-identified patent and that said Letters Patent is hereby corrected as shown below:

\*In claim 1, column 9, line 65, after "terminally sterilizing", delete "of".

In claim 5, column 10, line 18, "sterilisation" (both occurrences) should read --sterilization--.

In claim 6, column 10, line 21, "sterilisation" (both occurrences) should read --sterilization--.

In claim 7, column 10, line 24, "sterilisation," should read --sterilization,--.

In claim 7, column 10, line 25, "sterilised" should read --sterilized--.

In claim 7, column 10, line 26, "sterilised" should read --sterilized--.

In claim 7, column 10, line 27, "sterilised" should read --sterilized--.

In claim 16, column 10, line 50, "sterilisation is radiation sterilisation." should read --sterilization is radiation sterilization.--.

Signed and Sealed this

Twenty-third Day of November, 2010

David J. Kappos
*Director of the United States Patent and Trademark Office*